United States Patent [19]

Salyer

[11] Patent Number: 5,650,090
[45] Date of Patent: *Jul. 22, 1997

[54] COMPOSITIONS FOR THERMAL ENERGY STORAGE OR THERMAL ENERGY GENERATION

[75] Inventor: Ival O. Salyer, Dayton, Ohio

[73] Assignee: Phase Change Laboratories, Inc., San Diego, Calif.

[*] Notice: The term of this patent shall not extend beyond the expiration date of Pat. No. 5,423,996.

[21] Appl. No.: 583,554

[22] Filed: Jan. 5, 1996

Related U.S. Application Data

[63] Continuation of Ser. No. 456,950, Jun. 1, 1995, Pat. No. 5,552,075, and Ser. No. 228,147, Apr. 15, 1994, Pat. No. 5,423,996.

[51] Int. Cl.$^6$ .................................................. C09K 5/02
[52] U.S. Cl. ............... 252/70; 165/104.12; 165/104.21; 564/63; 564/73
[58] Field of Search ................ 252/70; 165/104.12, 165/104.21; 564/63, 73

[56] References Cited

U.S. PATENT DOCUMENTS

| | | | |
|---|---|---|---|
| 3,640,698 | 2/1972 | Backlund | 71/29 |
| 3,874,504 | 4/1975 | Verakas | 206/219 |
| 4,008,170 | 2/1977 | Allan | 252/194 |
| 4,025,444 | 5/1977 | Murphy et al. | 252/8.8 |
| 4,207,885 | 6/1980 | Hampton et al. | 128/156 |
| 4,237,023 | 12/1980 | Johnson et al. | 252/70 |
| 4,283,427 | 8/1981 | Winters et al. | 426/107 |
| 4,426,307 | 1/1984 | Wada et a. | 252/70 |
| 4,488,817 | 12/1984 | Uesaka et al. | 366/144 |
| 4,533,483 | 8/1985 | Watson et al. | 252/70 |
| 4,579,580 | 4/1986 | Moore | 71/28 |
| 4,659,629 | 4/1987 | Gartner et al. | 428/469 |
| 4,711,813 | 12/1987 | Salyer | 428/402 |
| 4,797,160 | 1/1989 | Salyer | 106/96 |
| 4,825,939 | 5/1989 | Salyer et al. | 156/53 |
| 4,988,543 | 1/1991 | Houle et al. | 427/372.2 |
| 5,028,270 | 7/1991 | Föster et al. | 106/35 |
| 5,053,446 | 10/1991 | Salyer et al. | 524/8 |
| 5,106,520 | 4/1992 | Salyer | 252/70 |
| 5,211,949 | 5/1993 | Salyer | 424/402 |
| 5,254,380 | 10/1993 | Salyer | 428/35.7 |
| 5,282,994 | 2/1994 | Salyer et al. | 252/70 |
| 5,423,996 | 6/1995 | Salyer | 252/70 |

Primary Examiner—Melissa Bonner
Attorney, Agent, or Firm—Killworth Gottman Hagan & Schaeff

[57] ABSTRACT

A composition for thermal energy storage or thermal energy generation comprising a silica based gel or dry powder in the form of silica particles containing a water/urea phase change material for thermal energy storage or an endothermic or exothermic compound for thermal energy generation. The water/urea phase change material stores and releases at least 50 cal/gm of thermal energy in freezing and melting, and has a melting and a freezing point in the range of −11° C. to −15° C. The endothermic compound is preferably ammonium nitrate, urea, or combinations thereof. The exothermic compound is preferably calcium oxide or calcium chloride. The thermal energy storage composition may find use in a variety of applications including medical wraps, food servingware, and "blue ice" for cold packs or food storage. The thermal energy generation composition may find use as medical wraps, food servingware, and refrigerators when endothermic and medical wraps, food servingware, heaters, stadium seats, boots, vests, caps ear muffs, and scarves when exothermic.

5 Claims, 5 Drawing Sheets

COMPOSITIONS FOR THERMAL ENERGY STORAGE OR THERMAL ENERGY GENERATION

CROSS-REFERENCE TO RELATED APPLICATION

This application is a continuation of U.S. application Ser. No. 08/456,950, filed Jun. 1, 1995, now U.S. Pat. No. 5,552,075, which in turn is a continuation of U.S. application Ser. No. 08/228,147, filed Apr. 15, 1994, which issued as U.S. Pat. No. 5,423,996, on Jun. 13, 1995.

BACKGROUND OF THE INVENTION

The present invention relates to compositions for thermal energy storage or thermal energy generation, and more particularly, to a composition comprising a silica based gel or dry powder containing a water/urea phase change material for thermal energy storage or an endothermic or exothermic compound for thermal energy generation.

Phase change materials may be repeatedly converted between solid and liquid phases and utilize their latent heat of fusion to absorb, store and release heat or cool during such phase conversions.

These latent heats of fusion are greater than the sensible heat capacities of the materials. For example, in phase change materials, the amount of energy absorbed upon melting or released upon freezing is much greater than the amount of energy absorbed or released upon increasing or decreasing the temperature of the material over an increment of 10° C.

Upon melting and freezing, per unit weight, a phase change material absorbs and releases substantially more energy than a sensible heat storage material that is heated or cooled over the same temperature range. In contrast to a sensible heat storage material that absorbs and releases energy essentially uniformly over a broad temperature range, a phase change material absorbs and releases a large quantity of energy in the vicinity of its melting/freezing point.

Ice/water phase change materials are low-cost, widely-used phase change materials for temperature regulation at 0° C. Such phase change materials have found use in applications such as refrigeration, chilling of beverages, medical therapy, and frozen confections. The many applications for ice/water phase change material could be significantly increased if a means could be found to decrease the freezing temperature without a prohibitive concurrent decrease in thermal energy storage. Soluble additives such as salt, alcohol, glycol, glycerine, or sugar, all function to depress the freezing point of water to temperatures well below 0° C. but these additives also decrease the heat of fusion to 50% or less that of pure water. Further, such additives, when mixed with ice/water, are messy and inconvenient to use.

If, for example, ice/water could be made to freeze and melt congruently at a temperature in the range of −11° to −15° C., without a substantial decrease in the heat of fusion and crystallization, many new applications would become possible and current applications improved. The new modified ice/water could be used to freeze pure water, make ice cream, keep cold drinks colder, store cool for off-peak electrical air conditioning, and thermal energy storage of "cool" for diurnal and seasonal cooling. Thus it could be used in a device for making frozen confections such as that disclosed in Uesaka, U.S. Pat. No. 4,488,817. Uesaka discloses using a cold-keeping agent which comprises water or carbonated water with organic or inorganic salts added thereto in a double-walled vessel for that purpose.

Further, if there were a means for containing the new modified ice/water so as to encapsulate it or to render it a dry powder, then, its use could be greatly expanded beyond that discussed above. In my U.S. Pat. Nos. 5,106,520 and 5,282,994 there is disclosed a free flowing, conformable powder-like mix of silica particles and a phase change material which may include water. Still there is no disclosure of the use of a water/urea clathrate or inclusion compound as the phase change material.

Thus, while phase change materials for thermal energy storage are known, improved thermal energy storage materials would be desirable. Likewise, improved endothermic and exothermic compounds for thermal energy generation are also in demand.

Instant cold and instant hot products for medical therapy and other uses are known. There are a number of instant cold packs on the market based on ammonium nitrate/water. These products usually contain a freezing point depressant (to prevent freezing to a hard ice in reuse); and, in some cases, a gelling agent as well to produce a somewhat reusable gel. One of the instant hot products commercially available is based on supercooling of a salt hydrate, sodium acetate trihydrate, that is initiated by mechanical attrition to start crystallization and supply hot at about 50° C. The product can be reactivated by remelting in boiling water to provide limited reuse capability as a gel. With both the instant cold and instant hot products, the reusable gel has only a limited effectiveness and a limited useful life. Accordingly, a gel with a superior reuse capability would be advantageous. Perhaps even more advantageous would be a dry powder containing an endothermic or exothermic compound because of its soft conformability. As discussed above, dry powders containing phase change materials are disclosed in my U.S. Pat. Nos. 5,106,520 and 5,282,994, but there is no disclosure of using endothermic or exothermic compounds in that regard.

Accordingly, there is still a need in the art for improved compositions useful in thermal energy storage or thermal energy generation which are inexpensive and easy to use.

SUMMARY OF THE INVENTION

The present invention meets that need by providing a silica based gel or dry powder in the form of silica particles containing a water/urea phase change material for thermal energy storage or an endothermic or exothermic compound for thermal energy generation. In one embodiment, there is provided a water/urea phase change material contained in a particulate silica matrix. Preferably, the silica particles are hydrophobic silica particles surface treated with 0.5–5 parts per hundred by weight of a silane coupling agent or silicone resin. The mixture of silica and phase change material (PCM) is preferably in the form of a free-flowing, conformable powder-like mix, i.e. PCM/silica dry powder, which may be prepared in accordance with U.S. Pat. Nos. 5,106,520 or 5,282,994, which are incorporated herein by reference. The water/urea PCM/silica dry powder preferably has a thermal energy storage of greater than 30 cal/gm.

In this embodiment, the silica is preferably present in an amount of from 30 to 40% by weight and the water/urea phase change material is present in an amount of from 70 to 60% by weight. This type of structure is especially desirable for medical wrap applications, but is of interest in other applications such as for tableware. Thus, the PCM/silica dry powder may be disposed in a liquid impervious polymer film or a metal foil enclosure to form a medical wrap. The PCM/silica dry powder may also be disposed in the plastic housing of containers such as tableware items or ice cream freezers.

Likewise, the water/urea phase change material/silica dry powder composition may be disposed in the inner chamber of a housing where the housing includes an inner cavity for containing a heat sensitive item such as a flight recorder. Such a device is disclosed in copending application Ser. No. 08/044,819, incorporated herein by reference.

The water/urea phase change material is a water/urea clathrate or inclusion compound which melts and freezes congruently in the range of about −11° C. to −15° C., and stores and releases over at least 50 cal/gram, preferably over 60 cal/gram, and up to 72 cal/gram of thermal energy in melting and freezing. The water/urea phase change material preferably is less than about 80% by weight water, preferably within the range of about 82–54.5%, and more preferably within the range 78–70%, and at least about 20% by weight urea, preferably within the range 18–44.5% and more preferably within the range 22–30%. In the most preferred embodiment, the water/urea phase change material is about 75% by weight water and about 25% by weight urea.

The thermal energy storage composition of the present invention is useful in a variety of applications. For example, the composition may be used in medical wraps, food servingware, and "blue ice" for cold packs or food storage.

The water/urea phase change material may also be used in neat form. For example, the water/urea phase change material by itself may be disposed in a bag or container made of a liquid impervious polymer for use as "blue ice" or it may be disposed in the plastic housing of containers such as tableware items or ice cream freezers.

In another embodiment, there is provided a silica based gel or dry powder composition capable of generating high endothermic cool or exothermic hot, when activated by a liquid activating solution, such as water. When water, or another phase change material is used as the liquid activating agent, the composition is thereafter capable of being reused as a thermal energy storage device. For a compound to supply high endothermic cooling or exothermic heating, the chemical must have a high negative or positive heat of solution in a liquid activating solution such as water, a relatively low molecular weight, combined with high solubility in a liquid activating solution such as water (at or near ambient temperature). Additionally, the chemical must be non-toxic, environmentally safe, and available at reasonable cost.

For instant cooling, ammonium nitrate, which has a high molal endothermic heat of solution, low molecular weight, and high solubility in water, is non-toxic and low-cost. Urea also has a relatively high endothermic heat of solution (second to ammonium nitrate), and is non-toxic and is environmentally acceptable.

Accordingly, in the preferred embodiment for instant cold applications ammonium nitrate, urea, and combinations of these two chemicals are used with hydrophilic fumed or precipitated silica particles, with and without a freezing point depressant, to produce a reusable gel at lower silica concentrations (i.e. 20 to 30% by weight of the total composition); and a soft, comformable dry powder at higher silica concentrations (i.e. 30 to 40% by weight of the total composition). In this system, salt can function as a freezing point depressant to provide reuse capability in the gels, but is not essential in the dry powder compositions that contain a high amount of silica. However, in the gels or dry powder the urea can supply significant added thermal energy storage if it is added in solid powder form and mixed with the ammonium nitrate prior to activating the system with water.

The gels will have reuse capability only as sensible heat materials, since a freezing point depressant is present to prevent freezing to a hard lump of "ice." The dry powder, on the other hand, can be reused as a phase change material if recharged by freezing, and without forming a hard lump of ice.

Most of the compositions having the highest exothermic heat of solution and highest solubility present obvious problems of toxicity, thermal instability, etc. The hydration of calcium oxide (lime) with water produces excessively high temperatures and forms a solid brick. Still, this vigorous exothermic reaction may be of interest as a high-temperature heat source for non-medical use. The preferred exothermic material for medical therapy applications is calcium chloride. Calcium chloride may, thus, be added to hydrophilic fumed or precipitated silica particles to form a gel at lower concentrations of silica (i.e. 15 to 25% by weight of the total composition) and dry powders at higher concentrations of silica (i.e. 25 to 40% by weight of the total composition). If desired, added temperature exotherm may be obtained by a combination of one highly exothermic compound such as calcium chloride and a second exothermic compound such as calcium oxide, potassium carbonate or others.

Suitable means for containing the separate dry and liquid activating solution ingredients must be provided for the instant cold and instant hot systems. Film containers in which the liquid activating solution such as water is contained in a "rupturable" bag inside a larger bag containing the dry ingredients is one system that is described in the U.S. Pat. No. 3,874,504, which is incorporated herein by reference, and which may be used. However, to avoid the possibility of accidental activation, the water may be contained in a separate small bag attached to the outside of the larger bag. To activate the system, the larger bag is opened and the water poured therein and rapidly mixed to produce an instant hot gel or dry powder.

The primary use of the instant cold and instant hot gels and dry powders is probably for medical therapy where they supply sensible energy on a time/temperature thermocline. In this use they may supplement the thermal energy storage material based on the water/urea phase change material of the first embodiment discussed above. The instant cold and instant hot gels and dry powders can be activated anytime and anyplace, and have reuse capability. Additional applications for which the instant cold and instant hot gels and dry powders may be used include clothing and wearing apparel, home ice cream freezing, outdoor cooking, and seasonal thermal storage.

Accordingly, it is an object of the present invention to provide a composition for thermal energy storage or thermal energy generation comprising a silica based gel or dry powder containing a water/urea phase change material for thermal energy storage or an endothermic or exothermic compound for thermal energy generation. These, and other objects and advantages of the present invention, will become apparent from the following detailed description and the accompanying claims.

DETAILED DESCRIPTION OF THE PREFERRED EMBODIMENT

Figure 1:
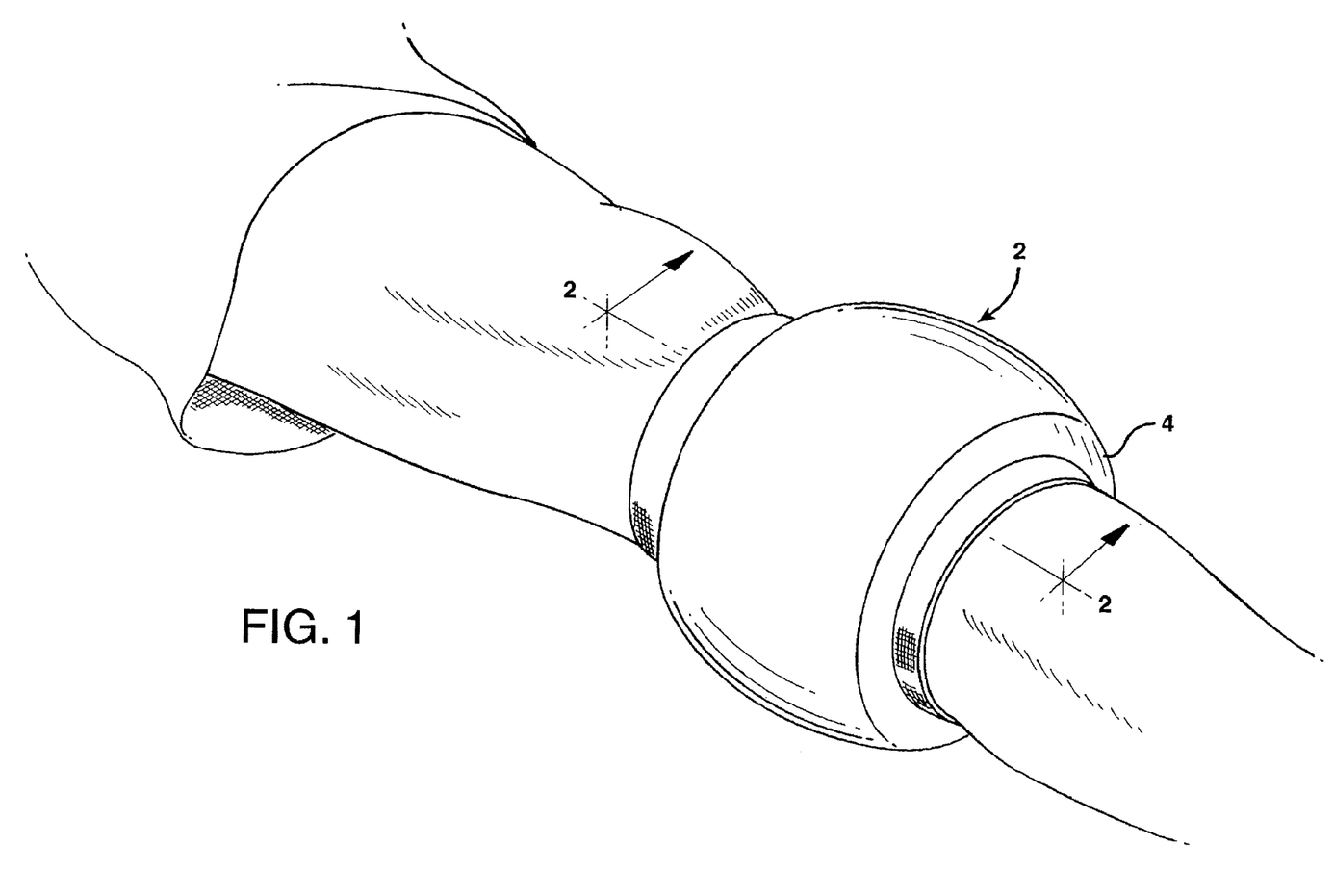
FIG. 1 is a diagrammatic view of a medical wrap utilizing the compositions of the invention.
Figure 2:
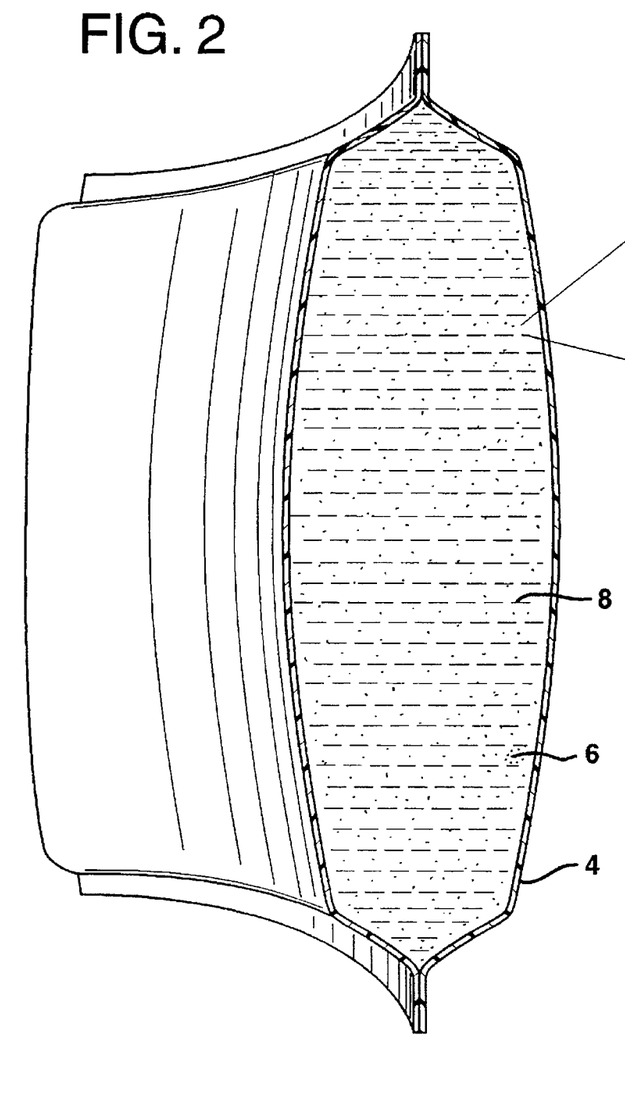
FIG. 2 is a sectional view taken along the lines and arrows 2—2 shown in FIG. 1 wherein a water/urea phase change material/silica dry powder composition of one embodiment of the present invention is contained.
Figure 2A:
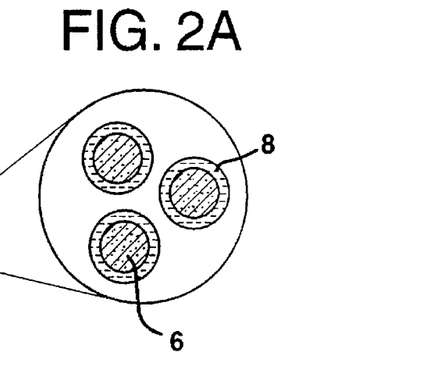
FIG. 2A is a magnified cut-away view showing the uniform nature of the water/urea phase change material/silica dry powder.
Figure 3A:
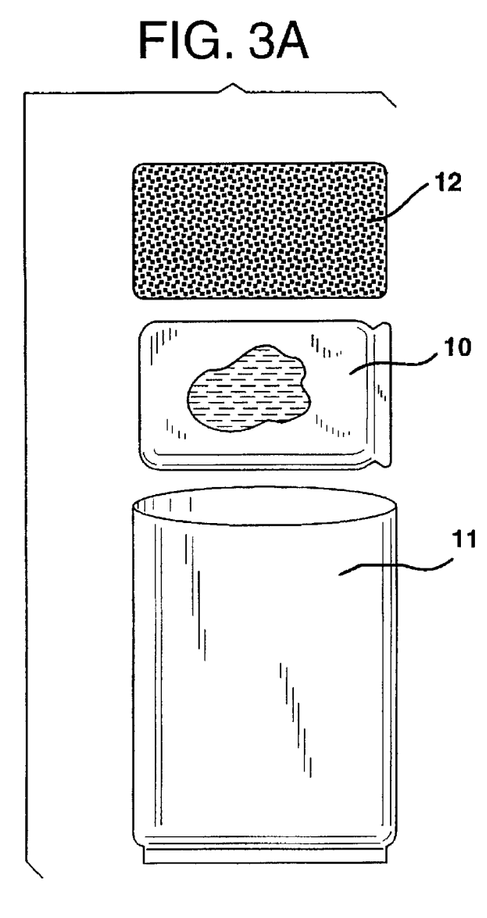
FIGS. 3A–3D show an elevational view, broken away, of formation of a pack for thermal energy generation utilizing the endothermic or exothermic compound/silica dry powder composition of another embodiment of the present invention.
Figure 3B:
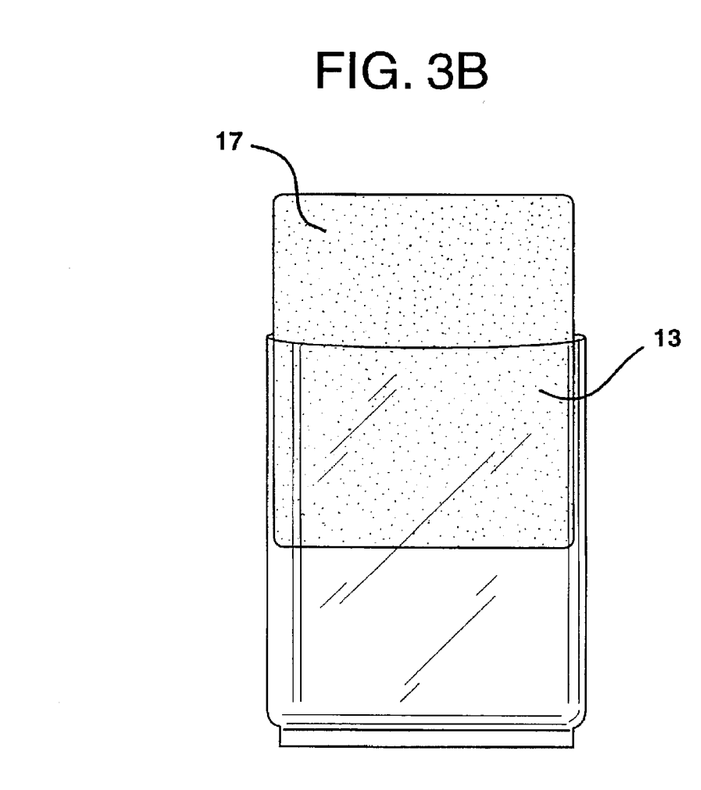
Figure 3C:
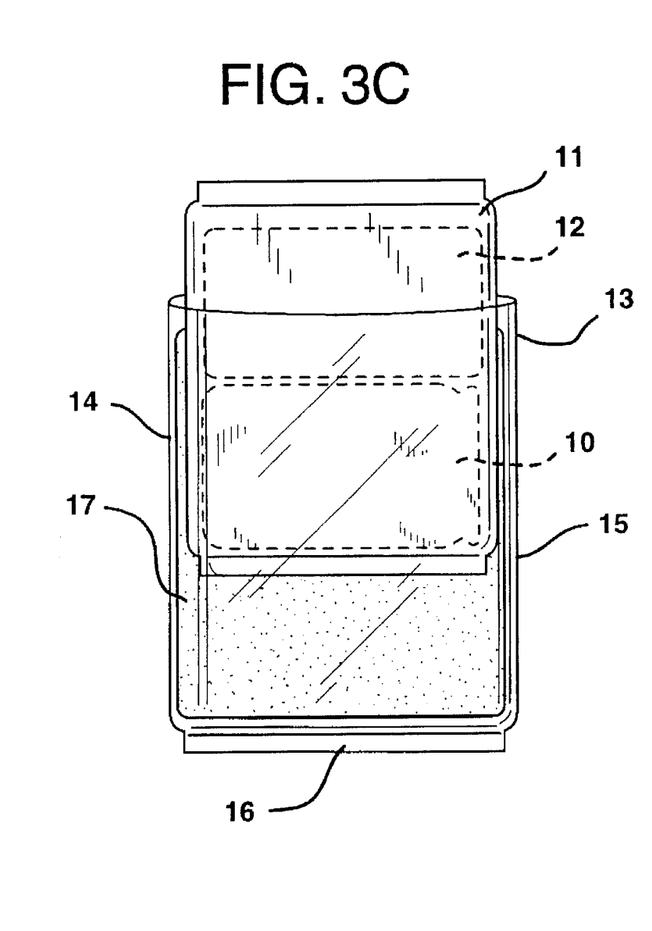
Figure 3D:
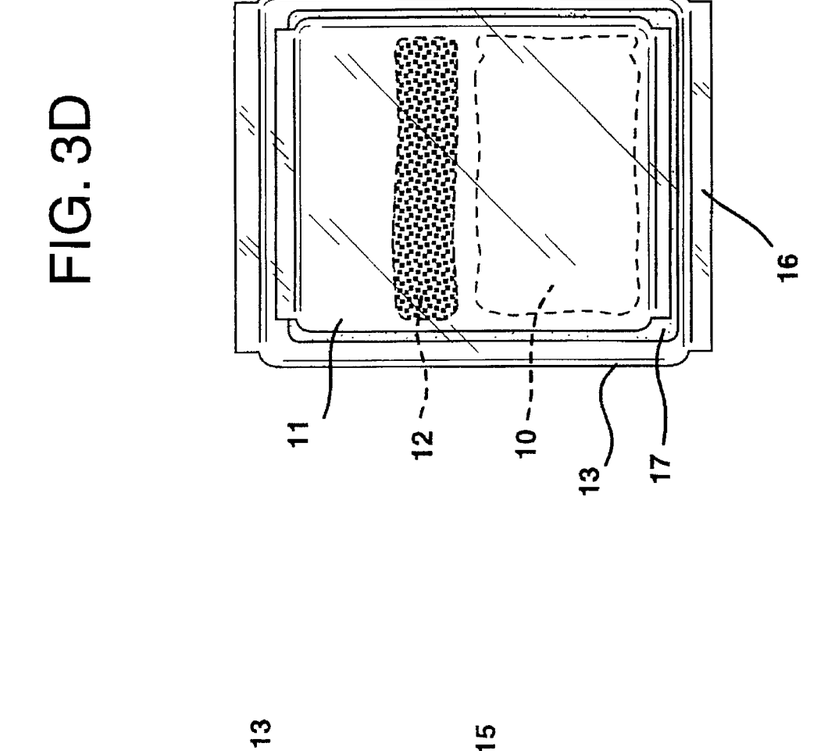

Referring now to the drawings, FIGS. 1, 2 and 2A show a medical wrap 2, specifically an elbow joint wrap, comprising an outer envelope 4, formed from a liquid impervious material which may be a polymeric material such as a butadiene-acrylonitrile copolymer, a polyester such as polyethylene terephthalate or vinyl polymer such as plasticized polyvinyl chloride, plasticized polyvinylidene chloride, low and high density polyethylene and ethylene-vinylacetate copolymers or a metal foil such as aluminum foil. Housed within the liquid impervious outer envelope is a powder-like mix comprising a silica matrix 8 containing a phase change material 6. The PCM/silica dry powder is shown diagrammatically only. In actual practice the phase change material is absorbed or adsorbed within and throughout the porous structure of the silica matrix. In any event the medical wrap 2 may also comprise fastener means such as "Velcro" strips (not shown) to provide for attachment of the wrap around the desired anatomical body part.

The preferred silica for use in the PCM/silica dry powder is a hydrophobic silica that has been surface treated with 0.5–5 pph (parts per hundred by weight) of a reacted silicone resin or a silane coupling agent such as dimethyldichlorosilane. As used herein in the specification and claims, hydrophobic silica is used to refer to a silica wherein the surface hydroxyl groups normally present have been reacted with silicone resins or silane coupling agents to form a less polar "hydrophobic" surface. The silica particles treated in such a manner may be either fumed silicas or precipitated silicas. Exemplary silicas include precipitated silicas such as those disclosed in U.S. Pat. Nos. 5,106,520 and 5,282,994, incorporated herein by reference. The preferred silica particle size is from about $7 \times 10^{-3}$ to about $7 \times 10^{-2}$ microns.

In FIGS. 3A–3D the liquid activating solution, such as water, for activating the endothermic or exothermic activity of the composition for thermal energy generation fills a small, sealed, liquid-tight inner bag 10 of suitable flexible plastic that is relatively easily ruptured by the liquid when squeezed manually. Inner bag 10, filed with the liquid activating solution is inserted into an open end of an open-topped intermediate envelope 11 which may be made of a liquid impervious material as in FIGS. 1, 2 and 2A. The remainder of envelope 11 is then filled or substantially filled with composition 12 of the present invention, in this instance a silica based dry powder containing an endothermic or exothermic compound for thermal energy generation. Following that, the top of intermediate envelope 11 is sealed. When the squeezing occurs, inner bag 10 is ruptured, enabling the liquid activating solution to mix with the silica based dry powder containing the endothermic or exothermic compound, causing the latter to absorb or release heat, depending on the type of material it is, but the activated mixture remains sealed in intermediate envelope 11.

After being filled, as described, and before being squeezed to absorb or release heat, the sealed intermediate envelope 11 is slidably inserted into an open-topped outer pouch 13, that is just slightly larger in size. Preferably, the outer pouch 13 is of flexible, transparent plastic, such as polyethylene or other impervious material as in FIGS. 1, 2 and 2A, and it is relatively flat, with its opposite major faces joined integrally to one another at the opposite side edges 14 and 15 and sealed to each other along the bottom of edge 16.

A thin, flat, flexible sheet 17 of heat insulation material may be inserted into the outer pouch 13 either before or after the insertion of the sealed intermediate envelope 11. This heat insulation sheet may be of fine cell or cross-linked polyethylene or other suitable material, and it extends substantially completely across the inside of one major face of the outer pouch 13 and separates this side of the pouch from the sealed intermediate envelope 11.

After both the insulation sheet 17 and the sealed inner envelope 11 have been inserted, the top of the outer pouch 13 is sealed to provide a liquid-tight package.

Preferably, the outer pouch 13 is of suitable flexible, transparent plastic and, in the absence of a defect, it does not rupture when squeezed manually. The outer pouch 13 constitutes a means for affixing the insulation sheet 17 to envelope 11. The affixing means could take other forms such as adhesive, but the outer pouch is preferred and advantageous. For example, the outer pouch provides extra protection against leakage.

Before using this instant cold or instant hot pack to either heat or cool, the pack provides a relatively flat package containing the sealed inner envelope 11 in which the particles of composition 12 are segregated from the liquid activating solution by the rupturable membrane constituted by the inner bag 10.

After the thermal energy generation upon first use, the mixture in intermediate envelope 11 may serve as a thermal energy storage device, and by heating or cooling the pack, as the case may be, it may be reused for medical therapy or other uses. Thus, the liquid activating agent may itself be a phase change material which not only activates the endothermic or exothermic compound, but is also absorbed or adsorbed by the silica particles so as to form a PCM/silica gel or dry powder capable of thermal energy storage upon reuse.

Figure 4:
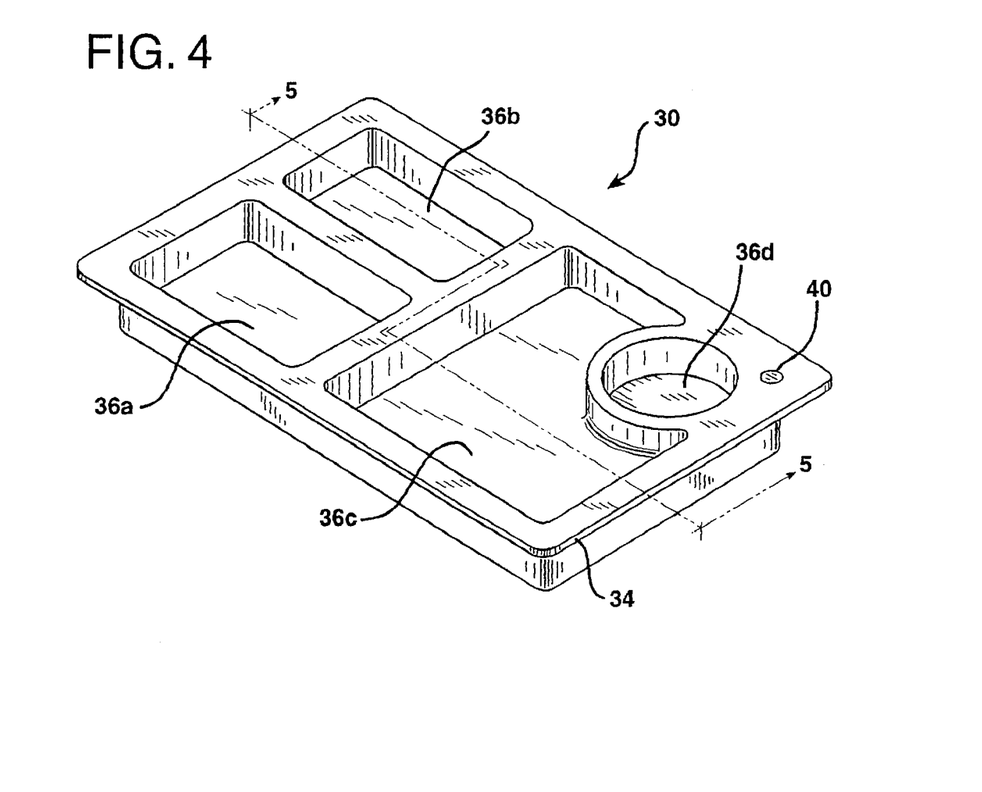
FIG. 4 is a diagrammatic view of a tableware item, a dinner serving tray, utilizing the compositions of the present invention.
Figure 5:
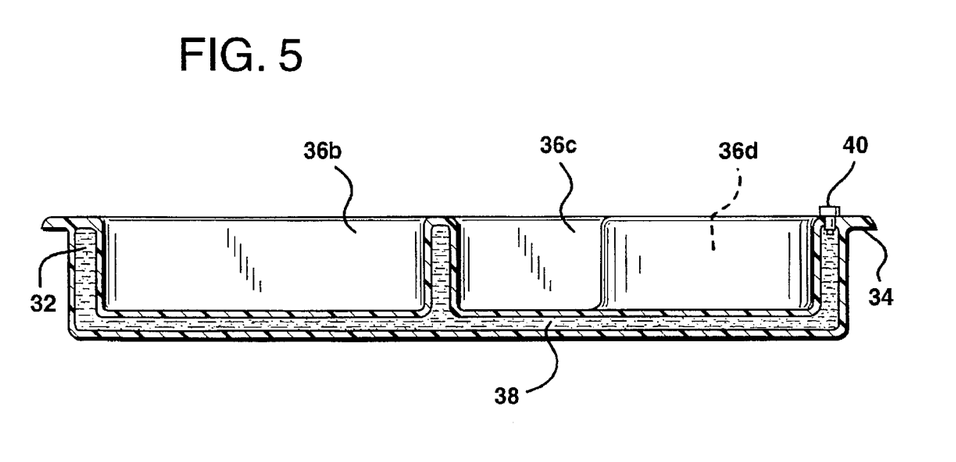
FIG. 5 is a sectional view taken along arrows 5—5 in FIG. 4.

FIGS. 4 and 5 depict a tableware item, a dinner serving tray 30 of the type used by airlines, etc. that incorporates the present composition disposed therein. Tray 30 comprises a plurality of compartments 36a–d to act as receptacles for food and a beverage container. Preferably, tray 30 comprises a plastic housing 34 that is filled with composition 38 of the present invention which in one embodiment is a water/urea PCM/silica dry powder composition and in another embodiment is a silica based dry powder containing an endothermic or exothermic compound. In that instance, a tap 40 may be used for addition of a liquid activating solution such as water in order to initiate the endothermic or exothermic reaction. Alternatively, a liquid activating solution such as water may be contained in cavity 32 separated from composition 38 by a rupturable divider (not shown), such as a rupturable membrane, which is ruptured to initiate the endothermic or exothermic reaction.

As with the embodiment employing a water/urea phase change material, other uses for an instant cold system, could be for ice cream freezers and other refrigeration devices. With the instant hot system, the device would be to heat food or drink. Other uses for an instant hot system of this type would be stadium seats, boots, vests, caps, ear muffs, scarves, etc.

In order that the invention may be more readily understood, reference is made to the following examples, which are intended to be illustrative of the invention, but are not intended to be limiting in scope.

EXAMPLE 1

This example illustrates the general laboratory procedure for preparing a water/urea clathrate or inclusion compound. Commercial chemical and medical grades of urea were mixed with water in ratios ranging from 90/10% water/urea by weight to 54.5/45.5% by weight. All of the samples except for the 54.5/45.5% ratio dissolved quickly at room temperature. This sample required heating to obtain a solution that did not appear to be complete when the sample cooled down to room temperature.

Analysis of thermal energy storage characteristics of the solutions was performed. The compositions containing water/urea in ratios of 30/1 down to 13/1 showed two distinct melting and freezing temperatures, one of which was essentially water, and the second apparently a clathrate or inclusion compound with a melting temperature of about $-11°$ C. and a freezing temperature of about $-15°$ C.

As the water content in the composition was decreased to water/urea 13/1 and lower, the melting and freezing attributed to a separate water phase disappeared altogether, and a single clathrate melting and freezing near $-11°$ C. and $-15°$ C. respectively remained. Further, the thermal energy storage characteristics of the water/urea phase change materials were about 70 cal/gm, which is close to the accepted value of 80 cal/gm attributed to water. Comparisons were made with water modified with ethanol at compositions of water/ethanol of 48/1 to 12/1. Such compositions exhibited normal freezing point depression and a progressively lower heat of fusion as more ethanol was added to bring the molar composition to water/ethanol 12/1.

The data regarding thermal energy storage characteristics is summarized in Tables 1 and 2. Wherein the differential scanning calorimetry (DSC) data includes the melting temperature in degrees centigrade (Tm° C.), the freezing temperature in degrees centigrade (Tc° C.), the difference between melting and freezing temperature (Tm–Tc° C.), the heat of fusion in calories per gram ($\Delta$Hf Cal/gm) and the heat of crystallization in calories per gram ($\Delta$Hc Cal/gm).

TABLE 1

| Material | Tm °C. | Tc °C. | Tm – Tc °C. | $\Delta$Hf Cal/gm | $\Delta$Hc Cal/gm |
|---|---|---|---|---|---|
| H$_2$O/EtOH 95/55 wt. 48.8/1 molar | –2.8 | –14.2 | 16.2 | 38.8 | 40.1 |
| H$_2$O/EtOH 90/10 wt. 23/1 molar | –5.7 | –15.3 | 9.6 | 30.6 | 31.5 |
| H$_2$O/EtOH 85/15 wt. 14.5/1 molar | –7.4 | –16.1 | 8.7 | 27.3 | 27.8 |
| H$_2$O/EtOH 82.5/17.5 12/1 molar | –10.8 | –21.6 | 10.8 | 22.1 | 22.0 |

TABLE 2

| Material | Tm °C. | Tc °C. | Tm – Tc °C. | $\Delta$Hf Cal/gm | $\Delta$Hc Cal/gm |
|---|---|---|---|---|---|
| Water/Urea 90/10 wt. 30/1 molar | –11.04 –3.37 | –20.80 –14.00 | 9.76 10.72 | 68.73 | 62.86 |
| Water/Urea 85/15 wt. 17.7/1 molar | –11.33 –6.99 | –23.49 –11.51 | 12.15 9.64 | 58.39 | 51.92 |
| Water/Urea 80/20 wt. 13.3/1 molar | –11.01 | –16.54 –14.73 | 5.62 3.32 | 62.79 | 59.76 |

EXAMPLE 2

Several samples of water/urea phase change material/hydrophilic silica (Cabot MS-7), i.e. PCM/silica dry powder, were prepared using the general mixing procedure described in related U.S. Pat. No. 5,282,994. The composition of the clathrate portion was varied to include water/urea ratios of 13.3/1, 13.0/1, 12.5/1 and 12.0/1. Free-flowing dry powders were formed in each case at PCM/silica compositions of 60/40% by weight. Thermal energy storage was analyzed by differential scanning calorimetry, and the data is shown in Table 4 in the same manner as the data, shown in Tables 1 and 2. It was observed that all of the samples showed an undesirable low freezing temperature of about $-25°$ C., versus about $-15°$ C. for the 100% clathrate of the same composition. Additionally, the thermal energy storage was at a significantly lower value of 30 cal/gram, whereas the storage predicted from the value of the neat water/urea phase change material, multiplied by the percentage of phase change material in the PCM/silica dry powder should have been about 40 cal/gram. It was concluded that the hydrophilic fumed silica was bonding with some of the water and thereby destroying the stoichiometry of the water/urea phase change material.

TABLE 4

| Material | Tm °C. | Tc °C. | Tm – Tc °C. | $\Delta$Hf Cal/gm | $\Delta$Hc Cal/gm |
|---|---|---|---|---|---|
| Water/Urea PCM 80/20 Wt. PCM/Silica 60/40 | –13.7 | –25.4 | 11.7 | 29.2 | 28.8 |

EXAMPLE 3

Using the general mixing procedure described in U.S. Pat. No. 5,282,994, a sample of water/urea phase change material (10/1 molar) was mixed with PPG BXS 318 from PPG Industries of Pittsburgh, Pa. (BXS-318) hydrophobic silica (treated with 1 pph silane coupling agent) to form a PCM/silica dry powder. The silica was added to the liquid water/urea phase change material at room temperature, and a free flowing dry powder was obtained at a composition of water/urea/BXS 318 of 67/33% by weight. Thermal energy storage was determined by differential scanning calorimetry, at a heating and cooling range of 2° C./minute. In contrast to the sample of similar water/urea/silica dry powder made with Cabot MS-7, the PCM/silica dry powder made with the PPG BXS 318 had a higher freezing temperature such as would be within the capacity of the ordinary freezers, or the

EXAMPLE 4

Instant cold packs, both of the prior art type, and of the type demonstrating the present invention were prepared as set forth in Table 6. Those prepared in accordance with the present invention, i.e. utilizing a silica based gel or dry powder, were prepared using hydrophilic precipitated silica particles from PPG Industries of Pittsburgh, Pa. (referred to as Silica ABS or ABS Silica) having a surface area of 150 m²/gram and an ultimate particle size of about 0.022 microns.

In Table 6, samples 17 and 18 show the prior art form of cold packs based on ammonium nitrate and water. Sample 18 contains seven parts of sodium chloride as a freezing point depressant. If salt were to be used, the concentration would need to be further increased (as in the commercial products) to prevent freezing to a hard lump of ice in reuse. Samples 19 and 20 both contain ABS silica sufficient to form a dry powder. Sample 20 dry powder contains additionally seven parts of NaCl freezing point depressant which is, in some respects, actually undesirable since it will make recharging by freezing, and reuse as a phase change material difficult. Accordingly, the composition of sample 19 without salt is preferred. Samples 21 and 22 of Table 6 both contain sufficient ABS silica to form a gel and the water used contains urea in the form of a water/urea (75/25) solution. This addition effectively prevents the gel from freezing to a hard ice at ordinary freezer temperatures and thus, provides reuse capability. An improved gel formulation is contained as Sample 26. In this case, the urea freezing point depressant is mixed directly into the ammonium nitrate prior to addition of the activating water. Since the urea adds further endothermic heat, this formulation may be preferred since it will go to lower temperatures and does not require any premixing of the urea with water (e.g. samples 21 and 22). The minimum temperature of Sample 26 is about 20° F. The minimum temperature for the sample 21 without the urea added to the dry powder is about 28° F.

Accordingly, this example shows endothermic compositions comprising ammonium nitrate, urea, or combinations of ammonium nitrate and urea with and without a freezing point depressant (salt or urea) and water plus sufficient hydrophilic (fumed or precipitated) silica to form a reusable gel (at lower silica concentrations) or a reusable dry powder (at higher concentrations) when activated with water.

TABLE 5

| Material | Tm °C. | Tc °C. | Tm − Tc °C. | ΔHf Cal/gm | ΔHc Cal/gm |
| --- | --- | --- | --- | --- | --- |
| Water/Urea (10/1) BXS-318 | −12.61 | −17.52 | 4.91 | 39.02 | 37.56 |
| Water/Urea (67.8/32.2) | −12.45 | −17.38 | 4.91 | 38.04 | 36.64 |

TABLE 6

INSTANT COLD PACKS BASED ON AMMONIUM NITRATE/ WATER FOR PHASE CHANGE LABORATORIES

| | One Use 17 | One Use 18 | Dry Powder 19 | Dry Powder 20 | Gel 21 | Gel 22 | Gel 26 |
| --- | --- | --- | --- | --- | --- | --- | --- |
| Water (gms) | 140 | 140 | 140 | 140 | — | — | 140 |
| Water/Urea (75/25) gms. | — | — | — | — | 187 | 187 | — |
| Urea gms. | — | — | — | — | — | — | 47 |
| Silica ABS gms. | — | — | 73.4 | 73.4 | 70 | 73.4 | 70 |
| Water/Silica % | — | — | 65/35 | 65/35 | 72.7/27.3 | 71.9/28.1 | 72/28 |
| $NH_4NO_3$ gms. | 168[1] | 168[1] | 168[2] | 168[2] | 168[2] | 168[2] | 168[2] |
| Salt (gms) | — | 7 | — | 7 | — | — | — |

[1] Ammonium Nitrate Prills (Pellets)
[2] Ammonium Nitrate Powder

EXAMPLE 5

Instant hot packs demonstrating the present invention were made as set forth in Table 7. The Silica ABS is the same as that discussed in Example 4.

The two hot packs include duplicates of a gel (No. 21) and dry powder (No. 23) respectively based on calcium chloride and ABS silica with water to activate. The gels give a higher maximum temperature, but the dry powders have better conformability. Maximum temperatures in the range of 155° to 145° F. were recorded for the gel and dry powder respectively.

Accordingly, this example shows a chemical composition for "instant hot" applications comprised of a high exothermic molal heat of solution compound having a relatively low molecular weight, a high solubility in water, plus hydrophilic silica in an amount sufficient to form a gel or a dry powder when subsequently mixed with separately contained water in ratios determined by the solubility of the exothermic compound in water.

TABLE 7

INSTANT HOT PACK BASED ON CALCIUM CHLORIDE/ WATER/SILICA

| | Sample Number | |
| --- | --- | --- |
| Sample Type (Gel or Dry Powder) | (21) Hot Pack Gel | (23) Hot Pack Dry Powder |
| 1. Water, distilled (gms) | 200 | 200 |
| 2. Ammonium Nitrate (gms) | | |
| 3. Calcium Chloride (gms) | 119 | 119 |
| 4. Silica ABS (gms) | 53 | 98.5 |
| 5. Water/Silica (%) | 79/21 | 67/33 |
| 6. Min. or Max. Temp. °F. | 155 | 147 |

The primary advantage is that the instant cold or instant hot reaction can be initiated by mixing with water anytime, anyplace, and the need for "charging" by prefreezing the instant cold or microwave heating the instant hot system is eliminated altogether. The primary disadvantage of the instant hot and instant cold gels and dry powders is that they cannot supply cold or heat for as long a time period as the comparable phase change materials, and the instant cold or hot is provided on a thermocline of ascending or descending temperature—not on a plateau of constant temperature as in the comparable phase change materials.

While certain representative embodiments and details have been shown for purposes of illustrating the invention, it will be apparent to those skilled in the art that various changes in the methods and apparatus disclosed herein may be made without departing from the scope of the invention., which is defined in the appended claims.

What is claimed is:

1. A composition for thermal energy storage consisting essentially of a water/urea phase change material, said water/urea phase change material being less than 80% by weight water and at least 20% by weight urea, said phase change material having a thermal energy storage of greater than 50 cal/gm and a melting and a freezing point in the range of −11° C. to −15° C.

2. The composition of claim 1 wherein said water/urea phase change material comprises less than 75% by weight water and at least 25% by weight urea.

3. The composition of claim 1 wherein said water/urea phase change material has a thermal energy storage of greater than 60 cal/gm.

4. An article for use in thermal energy storage comprising a container made of a liquid impervious material, said container having disposed therein a composition consisting essentially of a water/urea phase change material, said water/urea phase change material being less than 80% by weight water and at least 20% by weight urea, said phase change material having a thermal energy storage of greater than 50 cal/gm and a melting and freezing point in the range of −11° C. to −°15 C.

5. The article of claim 4 in which said liquid impervious material is a polymeric material.

* * * * *